United States Patent [19]

Milbrath et al.

[11] 4,385,046

[45] May 24, 1983

[54] DIAGNOSTIC RADIO-LABELED POLYSACCHARIDE DERIVATIVES

[75] Inventors: Dean S. Milbrath; Richard H. Ferber; William E. Barnett, all of St. Paul, Minn.

[73] Assignee: Minnesota Mining and Manufacturing Company, St. Paul, Minn.

[21] Appl. No.: 216,685

[22] Filed: Dec. 15, 1980

[51] Int. Cl.$^3$ ............... A61K 49/00; A61K 43/00; C08B 37/08

[52] U.S. Cl. ............................. 424/1; 424/9; 536/21

[58] Field of Search ................. 424/1, 9; 536/21

[56] References Cited

U.S. PATENT DOCUMENTS

| | | | |
|---|---|---|---|
| 2,959,583 | 11/1960 | Doczi | 536/21 |
| 3,118,816 | 1/1964 | Cushing | 167/74 |
| 3,118,817 | 1/1964 | Nomine et al. | 167/74 |
| 3,812,245 | 5/1974 | Dugan | 424/1 |
| 4,036,945 | 7/1977 | Haber | 424/1 |
| 4,057,617 | 11/1977 | Abramovici et al. | 424/1 |
| 4,124,705 | 11/1978 | Rothman et al. | 536/1 X |
| 4,126,669 | 11/1978 | Rothman et al. | 424/1 |
| 4,331,697 | 5/1982 | Kudo et al. | 536/21 |

FOREIGN PATENT DOCUMENTS

| | | | |
|---|---|---|---|
| 635463 | 11/1965 | Belgium . | |
| 55-161801 | 12/1980 | Japan | 536/21 |
| 2002406 | 2/1979 | United Kingdom | 563/21 |

OTHER PUBLICATIONS

Khan et al., Science, vol. 209, Jul. 11, 1980, pp. 295-297.
Thrombos, Haemostas., 41, pp. 450-453, 1979.
Padmakar V. Kulkarni et al., "Technetium-Labeled Heparin: Preliminary Report of a New Radiopharmaceutical with Potential for Imaging Damaged Cornorary Arteries and Myocardium", *J. Nucl. Med.*, 19, 810-815, (1979).
Padmakar V. Kulkarni et al., "Modified Technetium-99m Heparin for the Imaging of Acute Experimental Myocardial Infarcts", *J. Nucl. Med.*, 21, 117 (1980).
J. P. Esquerre et al., "Kinetics of Technetium-labeled Heparin in Thromboembolism: Preliminary Report", *Int. J. Nucl. Med. and Biol.*, 6, 215 (1979).
Kenneth A. Krohn et al., "Radiopharmaceuticals for Thrombus Detection: Selection, Preparation, and Critical Evaluation:" *Seminars in Nuclear Medicine*, 7, #3, 219 (1977).
L. Velluz, G. Nomine, and A. Pierdet, *C. R. Acad. Sci.*, 247, (1958) 1521-1523.
M. L. Wolfrom and R. Montgomery, *J. Am. Chem. Soc.*, 72 (1950) 2859-2861.
I. Danishefsky, H. B. Eiber, and J. J. Carr, *Arch. Biochem. Biophys.*, 90 (1960) 114-121.
C. Plotka and R. Jequier, *Arch. Int. Pharmacodyn, Ther.*, 126 (1960) 140-153.
L. Velluz, C. Platka and G. Nomine, *C. R. Acad. Sci.*, 247 (1958) 2203-2204.
S. Hirano and W. Ohaski, *Carbohydr. Res.*, 59 (1977) 285-288.
J. Kiss, *Heparin: Chemistry and Clinical Usage*, Ed. V. V. Kakkar and D. P. Thomas, Academic Press, London, 1976, p. 9.
Inoue et al., *Carbohydrate Research*, 46, 87-95 (1976).
Gary E. Krejacrek et al., "Covalent Attachment of Chelating Groups to Macromolecules," *Biochemical and Biophysical Research Communications*, 77, #2, 581 (1977).

*Primary Examiner*—Christine M. Nucker
*Attorney, Agent, or Firm*—Cruzan Alexander; Donald M. Sell; Lorraine R. Sherman

[57] ABSTRACT

A novel class of chelated radio-labeled polysaccharide derivatives are useful for diagnosing formed, and forming, blood clots in a vascular system. Novel intermediate metal-binding compounds comprise a water-soluble polysaccharide moiety having an average of at least 0.25 anionic groups per monosaccharide unit, and at least one chelating group derived from amino acids, substituted cyclic acid anhydrides, or carbon disulfide. The intermediate compound is then reacted with a radioactive tracer metal compound.

25 Claims, No Drawings

DIAGNOSTIC RADIO-LABELED POLYSACCHARIDE DERIVATIVES

TECHNICAL FIELD

This invention relates to a novel class of radioisotope-labeled polysaccharide derivatives useful for the diagnosis of blood clots. In another aspect, the invention relates to a method for locating a blood clot in a vascular system.

BACKGROUND ART

Vascular thrombosis, particularly in the deep veins of the leg, is a common medical disorder. A thrombosis often creates a great deal of localized pain and discomfort, and if the thrombus becomes dislodged, the resulting embolus may reach the capillary bed of the lung and create a life-threatening situation. Prompt diagnosis and treatment of vascular thrombi can greatly reduce the mortality rate from pulmonary embolism. Several major techniques for the diagnosis of vascular thrombi are known in the art, all of which suffer from various shortcomings.

The International Subcommittee on Diagnostic, Prophylaxis and Treatment of Venous Thrombosis noted in 1979 that "there is a need to develop improved noninvasive methods for the diagnosis of calf vein thrombosis in clinically symptomatic patients" and "current diagnostic tests are not useful for screening asymptomatic patients (other than $^{125}$I-fibrinogen leg scanning) and do not have predictive capacities" (Thrombos. Haemostas., 41, pp. 450–53, 1979).

Plethysmographic and Doppler ultrasound techniques which measures blood volume, blood pressure, or blood flow changes lack sufficient sensitivity to detect partially occluded vessels since substantial occlusion of major vessels is required to produce abnormal results. In addition, the source of the obstruction, i.e., thrombus, inflammation, swollen gland, etc., is not identified.

Contrast media radiography (venography, phlebography or angiography) is probably the most acceptable of the standard techniques available. Drawbacks of this procedure include the pain experienced by the patient and a significant number of other side effects ranging from thrombosis and allergic reactions to death. Many of these side effects have been eliminated with radionuclide venography and angiography although these techniques are expensive and the results are highly dependent on the skill of the individuals performing the techniques.

The above-mentioned techniques merely infer the location and size of a thrombus by the absence of blood flow or a "negative image". A better method would directly detect a thrombus by a "positive image". This has been done using $^{131}$I-fibrinogen which is incorporated biochemically into a growing thrombus producing a "hot" spot or "positive radiographic image". Unfortunately this material is only selective for actively growing thrombi and does not detect aged or nongrowing ones. The latter are the more common type of thrombi which a physician sees in symptomatic patients.

The desirability of a "positive radiographic image" technique has been well recognized. A number of thrombus-specific biomolecules such as urokinase, streptokinase and plasminogen, have been labeled with $^{99m}$Tc and tested in animals, but the results have not been reproducible. It is speculated that the variability of these results is caused by difficulties in protein isolation and variability in labeling techniques. Heparin labeled in this manner has been reported to image damaged coronary arteries and myocardium [Padmakar V. Kulkarni et al., "Technetium-Labeled Heparin: Preliminary Report of a New Radiopharmaceutical with Potential for Imaging Damaged Coronary Arteries and Myocardium", J. Nucl. Med., 19, 810–815 (1978) and Padmakar V. Kulkarni et al., "Modified Technetium-99m Heparin for the Imaging of Acute Experimental Myocardial Infarcts", J. Nucl. Med., 21, 117 (1980)]. $^{99m}$Tc-heparin is also being investigated for imaging damaged blood vessel walls by following pathologic changes in heparin clearance from the blood [J. P. Esquerre et al., "Kinetics of Technetium-labeled Heparin in Thromboembolism: Preliminary Report", Int. J. Nucl. Med. and Biol., 6, 215 (1979)].

Radio-labeled fibrinogen is a positive-imaging diagnostic agent for growing thrombi but has the definite limitation in that fibrinogen is derived from human blood, and therefore, offers the possibility of contamination by a hepatitus virus. See Kenneth A. Krohn et al., "Radiopharmaceuticals for Thrombus Detection: Selection, Preparation, and Critical Evaluation", Seminars in Nuclear Medicine, 7, #3, 219 (1977). A method for labeling fibrinogen and immunoglobulins with 99m-technetium is disclosed in U.S. Pat. No. 4,057,617.

Additional radio-labeled positive-imaging diagnostic preparations are taught in the patent literature. The novel compositions described in U.S. Pat. No. 3,812,245 are radio-labeled enzymes, $^{99m}$Tc-streptokinase and urokinase, stated to be useful for radiotracer localization of thromboembolisms in a vascular system. Radioactive-labeled antibodies for determining the size and location of myocardial infarcts is taught in U.S. Pat. No. 4,036,945.

In the prior art, certain chelating groups have been attached to heparin. U.S. Pat. No. 3,118,816 discloses an N-succinyl heparin which effects lipemia clearance and cholesterol lowering of the blood of warm-blooded animals, yet is substantially free of anticoagulant activity. U.S. Pat. No. 3,118,817 discloses N-(disulphobenzoyl) heparin which exhibits anticoagulant activity. Belg. Pat. No. 635,463 discloses N-(sulphobenzoyl) heparin, an anticogulant. N-benzoylheparin (L. Velluz, G. Nomine, and A. Pierdet, C. R. Acad. Sci., 247 (1958) 1521–1523), N-acetyl heparin (M. L. Wolfrom and R. Montgomery, J. Am. Chem. Soc., 72 (1950) 2859–2861) and (I. Danishefsky, H. B. Eiber, and J. J. Carr. Arch. Biochem. Biophys., 90 (1960) 114–121), N-(3,5-dimethylbenzoyl) heparin (C. Plotka and R. Jequier, Arch. Int. Pharmacodyn. Ther., 126 (1960) 140–153) and (L. Velluz, C. Platka, and G. Nomine, C. R. Acad. Sci., 247 (1958) 2203–2204), and N-acyl derivatives of heparin (S. Hirano and W. Ohashi, Carbohydr. Res., 59 (1977) 285–288) are also known. It appears novel in the art, however, to couple radioactive metal ions with chelate group-containing heparin compounds for use in locating a blood clot in a vascular system.

There remains a need in the art for imaging "aged" or formed thrombi, particularly those that are present in deep veins.

It is surprising that chelated heparin derivatives are attached to thrombi since it is known that desulfation of heparin reduces its anticoagulant activity and one would infer that it, therefore, would have little affinity for thrombi (J. Kiss, Heparin: Chemistry and Clinical

*Usage*, Ed. V. V. Kakkar and D. P. Thomas, Academic Press, London, 1976, p. 9).

DISCLOSURE OF INVENTION

This invention provides a radiopharmaceutical compound for diagnosing blood clots comprising the reaction product of (1) a metal-binding intermediate compound formed by the reaction of
  (a) a water-soluble polysaccharide having an average of at least 0.25 anionic groups per monosaccharide unit, and
  (b) at least one chelating agent capable of reacting with said polysaccharide without substantially affecting its chelating ability, and (2) a radioactive tracer metal compound.

In another aspect, the present invention provides a metal-binding intermediate compound for preparing a radio-pharmaceutical for diagnosing blood clots comprising a reaction product of (a) a water-soluble polysaccharide having an average of at least 0.25 anionic groups per monosaccharide unit, and (b) at least one chelating agent capable of reacting with said polysaccharide without substantially affecting its chelating ability.

In a further aspect, a method is provided for localizing and imaging an arterial or venous thrombus or embolus by means of the novel chelated radio-labeled polysaccharide derivatives of the present invention. The method of the invention detects not only actively growing, but also aged or nongrowing deep venous or arterial thrombi. In addition, the compositions of the present invention appear to be very stable.

"Polysaccharide" refers to a carbohydrate that, upon hydrolysis, yields exclusively or chiefly monosaccharides or products related to monosaccharides.

"Monosaccharides" are polyhydroxyaldehydes and polyhydroxyketones of 3 to 7 carbon atoms.

A chelating agent of the present invention provides at least two ligands capable of bonding with a radioactive metal ion.

Suitable polysaccharides include homopolysaccharides such as dextran sulfates (sulfated poly-1,6-glucose of various molecular weights), and heteropolysaccharides such as chondroitin sulfates A and C, dermatan sulfate, keratan sulfates I and II, heparin sulfate, and heparin. Heteropolysaccharides of the present invention contain sulfated disaccharide units such as D-glucosamine and D-glucuronic acid, D-glucosamine and L-iduronic acid, D-glucosamine and D-galactose, and D-galactosamine and D-galactose, having 1,3- and- /or 1,4-linkages. The preferred polysaccharide is heparin.

Heparin salt (often designated simply heparin) consists of mucopolysaccharides composed of D-glucosamine and D-uronic acid residues. Heparin salt mucopolysaccharides have molecular weights ranging up to about 30,000 and can be separated into fractions having number average molecular weights from about 3,000 to 15,000 or higher. Units of heparin salt have the structural formula (configurational placement of the groups not shown)

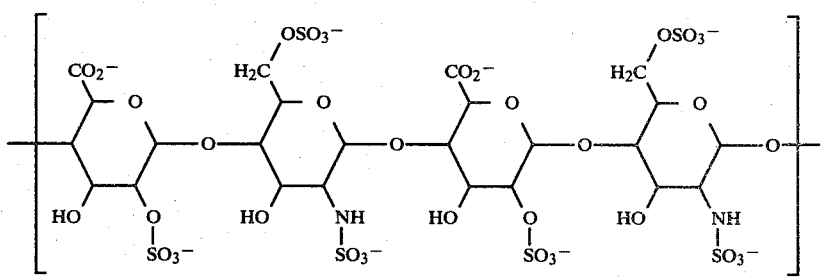

Formula I (plus cations to balance anionic charge)

The cations are generally sodium or calcium and neutralize the charge of the mucopolysaccharides. Individual mucopolysaccharides have from about 2 to about 25, and an average of about 15, of such units. In the following, for brevity, the formula for heparin anion is designated:

$R(NHSO_3^-)_a$          formula II in which:

"R" is the residue of the heparin anion devoid its $NHSO_3^-$ groups, and

"a" is a number having a value from about 5 to 50 and an average value of about 30.

"Heparinoid" means a derivative of heparin.

"Thrombus" means a clot of blood, either venous or arterial, formed within a blood vessel and remaining attached to its place of origin.

"Embolus" means a clot of blood that has broken from a thrombus and is floating free in the blood vessels or lodged at a site other than its site of formation.

The blood clot-specific materials of the present invention are radio-labeled polysaccharide derivatives. To form the metal-binding intermediate compounds, generally the homopolysaccharide or heteropolysaccharide is first modified by selectively removing N-sulfate groups to varying extents (i.e., up to 100%) and replacing them with chelating moieties such as residues formed from amino acids, cyclic acid anhydrides or carbon disulfide. Where the homopolysaccharides and heteropolysaccharides do not have N-sulfate groups (e.g., chondroitin, dextran sulfate, inulin sulfate and pentasan sulfate), the metal-binding intermediate compound is prepared by reaction of the polysaccharide with the chelating agent without the necessity of the preliminary N-desulfation step. Such novel intermediate metal-binding polysaccharide derivatives are also included within the scope of the present invention. A multiplicity of radioactive metal ions are susceptible to being coupled by common means to these intermediate chelating compounds.

As mentioned above, heparin is the preferred polysaccharide. The preferred chelating moieties are residues formed from diethylenetriamine pentaacetic acid (DTPA) and carbon disulfide (CS$_2$). Both heparin-DTPA and heparin-CS$_2$ bind the radioactive isotope with high efficiency and appear to be stable when incubated with normal plasma.

DETAILED DESCRIPTION

The present invention provides a diagnostic radio-labeled polysaccharide compound formed by the reaction of (a) a metal-binding polysaccharide intermediate reaction product of (1) a homopolysaccharide or a heteropolysaccharide, and (2) at least one chelating agent capable of reacting with polysaccharide hydroxyl or amino groups without affecting its chelating ability, the chelating agent being selected from amino acids, cyclic acid anhydrides, and carbon disulfide, and (b) a radioactive tracer metal compound which preferably is 111-indium chloride or a reduced 99m-pertectnetate salt.

The preferred embodiment of the present invention provides a diagnostic radio-labeled heparinoid compound comprising the reaction product of:

(a) a metal-binding heparinoid intermediate reaction product of (1) a heparin amine compound, formed by the removal of 10 to 100%, preferably 30-70%, and most preferably 40-60%, of the N-sulfate groups of heparin producing free amino groups, and (2) at least one chelating agent capable of reacting with the heparin amine compound without substantially affecting its chelating ability, such as amino acids, cyclic acid anhydrides, and carbon disulfide, and (b) a radioactive tracer metal compound, which preferably is 111-indium chloride or a reduced 99m-pertechnetate salt (i.e., a γ-ray emitter suitable for imaging).

The novel chelating intermediate product of step (a) above, wherein the chelating group is provided by an amino acid, a substituted cyclic acid anhydride, or carbon disulfide, is also provided by the present invention.

Heparin is commercially available from a number of pharmaceutical houses as the sodium or calcium salt.

The radio-labeled heparinoid compounds of the invention are prepared from a heparin salt by the following series of steps:

1. N-desulfation of heparin salt to form heparin amine,
2. coupling the heparin amine to the chelating moiety to prepare a metal-binding heparinoid intermediate compound, and
3. reacting the metal-binding heparinoid intermediate compound with a radioactive metal compound to form the radio-labeled heparinoid compound.

Radio-labeled heparinoid compounds prepared from any cyclic acid anhydride is provided by the present invention. However, with respect to the novel chelating heparinoid intermediate compounds provided by the present invention, the anhydrides used in their preparation are substituted cyclic acid anhydrides, such as acetoxy, acetamido, or acetothio derivatives of succinic, glutaric, adipic, or pimelic acid.

STEP 1. N-DESULFATION OF HEPARIN SALT

Heparin salt is N-desulfated to various extents by methods known in the art in accordance with the chemical equation:

Equation I

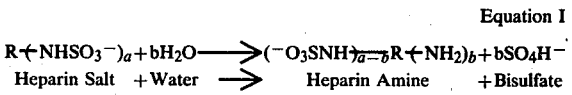

Heparin Salt + Water ⟶ Heparin Amine + Bisulfate in which a and b are numbers having a value from about 5 to 50, b is less than or equal to a, and R is the residue of heparin salt devoid its NHSO$_3^-$ groups as defined above. A preferable method for N-desulfation of heparin salt which avoids the possibility of depolymerization of the heparin molecules is described by Inoue et al., *Carbohydrate Research*, 46, 87-95 (1976) which teaches that heparin salt is ion exchanged using the acid form of a cation exchange resin such as Amberlite IR-120 ® (available from Rohm and Haas Co.), followed by neutralization of the effluent with an excess of tertiary amine (preferably pyridine). The tertiary amine salt of heparin is isolated (preferably by freeze-drying) and one part of the salt is then heated at a temperature of 20° to 75° C. for one to five hours in 15 to 20 parts by weight of an aprotic polar solvent such as dimethyl sulfoxide containing 1 to 10% water. The lower temperatures and shorter reaction times produce less N-desulfation of the heparin salt; the higher temperatures and longer times bring about removal of up to essentially 100% of the SO$_3^=$ groups from heparin. The N-desulfated heparin is then isolated by: (1) diluting the heated solution with 10% aqueous sodium chloride and adding the diluted solution to acetone to precipitate desulfated heparin and sodium chloride, (2) taking up the precipitate in aqueous sodium chloride and reprecipitating in acetone to remove aprotic polar solvent, and (3) dialyzing an aqueous solution of the precipitate to remove low molecular weight salts and freeze-drying the dialysate to obtain heparin amine.

The net result of this treatment is the conversion of the —NH—SO$_3^-$ groups to —NH$_2$ (see EXAMPLE 1).

STEP 2. PREPARATION OF METAL-BINDING HEPARINOID COMPOUNDS (COUPLING OF CHELATING MOIETIES TO THE AMINO GROUPS)

Metal-binding heparinoid compounds are prepared by the reaction of heparin amine and an acid or cyclic acid anhydride group-containing-multidentate compound in accordance with the chemical equation:

Equation II

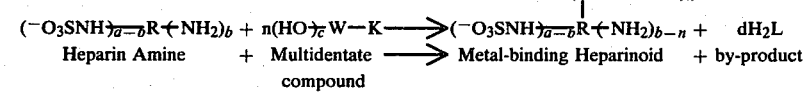

Heparin Amine + Multidentate compound ⟶ Metal-binding Heparinoid + by-product in which:
a, b, and R are defined above;
n is a number having a value of 1 to 50;
(HO)$_c$W—K is a chelating moiety in which c is 0 or 1, c being 1 when the chelating moiety is an acid and c being 0 when the chelating moiety is a cyclic acid anhydride;
d is n when c is 1 and d is zero when c is zero, and L is O (oxygen) except that when W is

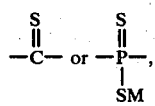

then L is S (sulfur);

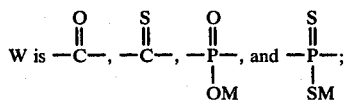

K is a coordinating ligand selected from the groups consisting of:
(a) $-(CH_2)_p N-(R^1)_2$
in which:
each $R^1$ is independently selected from the group consisting of
(1) hydrogen,
(2) $-(CH_2)_p-Y$, in which Y is

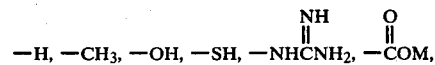

(3) $-(CH_2)_p-N-(R^1)_2$, and
p is an integer of 1 to 3, and
M is hydrogen, an alkali metal ion, ammonium ion or a lower alkyl group having 1 to 4 carbon atoms,
with the proviso that K contains no more than 4 nitrogen atoms and no nitrogen atom in K has more than one $-(CH_2)_p-Y$ groups in which Y is —H or —$CH_3$;
(b)

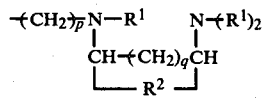

in which:
p and $R^1$ are as defined in (a),
q is 0 or 1 to 3, and $R^2$ is a divalent group having 2 to 6 carbon atoms, of which one carbon atoms can be replaced by —O—, —S—, or —NH—, which atoms are necessary in order to form a ring with —CH—$(CH_2)_q$CH—, the ring having 5 to 8 nuclear atoms that can be saturated or unsaturated and optionally substituted by $-(CH_2)_q-Y$ groups in which Y is as defined in (a) and q is 0 or 1 to 4;
(c)

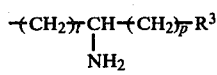

in which:
t is an integer of 0 or 1,
p is an integer of 1 to 3,
$R^3$ is a group selected from

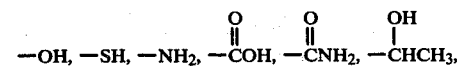

-continued

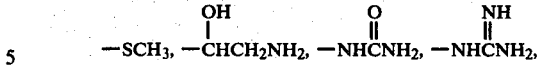

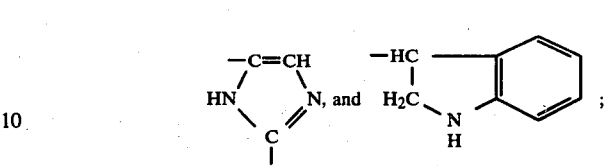

(d) $[-(CH_2)_r-O-]_s R^4$
in which:
r and s are independently integers of 1 to 4, and
$R^4$ is hydrogen or lower alkyl of 1 to 4 carbon atoms;
(e)

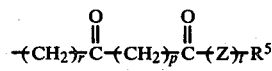

in which:
r, p, and t are integers of 1 to 4, 1 to 3, and 0 or 1 respectively,
Z is —O—, —S—, or —NH—, and
$R^5$ is a lower alkyl group having 1 to 4 carbon atoms;
(f)

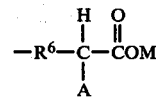

in which:
$R^6$ is alkylene or alkenylene having 1 to 4 carbon atoms,
M is as defined in (a), and
A is

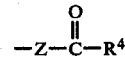

in which $R^4$ and Z are as defined in (d) and (e) respectively; and
(g)

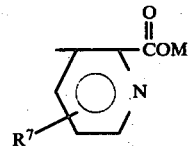

in which:
$R^7$ is $-(CH_2)_q-Y$ in which q is 0 or 1 to 4 and Y and M are as defined in (a).

STEP. 3. PREPARATION OF THE RADIO-LABELED HEPARINOID COMPOUNDS

The radio-labeled heparinoid compounds are prepared by the reaction of any radioactive tracer metal ion-containing salt with the metal-binding heparinoid of Step 2 in accordance with the chemical equation:

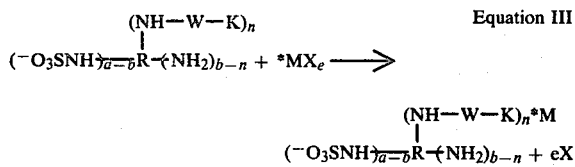

Equation III in which:
a, b, n, R, W and K are defined above,
*M is a radioactive tracer metal ion having a valence of e,
X is an anion such as chloride, bromide, sulfate, nitrate, and
e is an integer of 1 to 7.

The reaction may be carried out by adding an aqueous solution of any radioactive tracer metal ion-containing salt, preferably the halides of $^{111}$In, $^{68}$Ga, and $^{51}$Cr or the reduced form of $^{99m}$TcO$_4^-$ salts having an activity greater than about 2 millicuries per milliliter to a solution of the metal-binding heparinoid in water at a concentration of about 0.1 mg/ml up to 50 mg/ml and a pH of 2.0 to 5.0. The solution is then maintained, preferably stirred, at room temperature for from several minutes to 5 hours, and its pH adjusted to 7.2 to 7.4 with 0.2 M sodium bicarbonate. Generally, the reaction is carried out by adding the tracer metal salt solution to a solution of the metal-binding heparinoid compound at a concentration of 0.1 to 10.0 mg/ml in 0.9% weight-/volume saline solution having a pH of 2.0 to 5.0 to provide to the mixed solution an activity of about 0.2 to 10 mC/ml. After stirring the reactants to thoroughly mix the components and adjusting the pH of the solution to 7.2–7.4, the composition is ready for use. The radio-labeled heparinoid compounds of the invention, however, may be isolated by dialysis to remove low molecular weight salts and then freeze dried.

Suitable chelating moieties, (HO$\rightarrow$)$_c$W-K, where c is 1 and the coordinating ligand in (a) or (b) for use in the preparation of metal-binding heparinoid compounds in accordance with Equation II include the aminocarboxylic acids such as iminodiacetic, nitrilotriacetic, iminodipropionic, ethylenediaminodiacetic, ethylenediaminetriacetic, ethylenediaminetetraacetic, 1,3-propylenediaminetriacetic, 1,4-tetramethylenediaminetetraacetic, 1,4-cyclohexylenediaminetetraacetic, 1,6-hexylenediaminetetraacetic, diethylenetriamine-N,N',N"-triacetic, diethylenetriaminepentaacetic, dipropylenetriaminepentaacetic, aminophosphonic acids such as iminodi(methylenephosphonic), ethylenediaminodi(methylenephosphonic), and ethylenediaminetetra(methylenephosphonic); the aminothiocarboxylic acids such as diethylenetriaminepenta(methylenethiophosphonic); the carboxy-substituted amino compounds such as 1,4-bis[(carboxymethyl-2-hydroxyethyl)amino]cyclohexane, 1,4-bis[(carboxymethyl-2-mercaptoethyl)amino]cyclohexane, 1,2-bis[carboxymethyl-4[di(carboxymethyl)aminophenyl]amino]ethane, 1,2-bis[di(carboxymethyl)amino]cycloheptane, 2-[di(carboxymethyl)amino]tetrahydrofurane, 2-[di(carboxymethyl)amino]tetrahydrothiofurane, and 2-[di(carboxymethyl)amino]pyridine; and the corresponding sodium and potassium salts and the methyl, ethyl, propyl, and butyl esters of the above mentioned acids.

The chelating moieties (a) and (b) are reacted with heparin amine in accordance with Equation II by one of four methods commonly used in peptide synthesis. See, Gary E. Krejcarek et al., "Covalent Attachment of Chelating Groups to Macromolecules," *Biochemical and Biophysical Research Communications*, 77, #2, 581 (1977), and Ban An Khaw et al., "Myocardial Infarct Imaging of Antibodies to Canine Cardiac Myosin with Indium-111-Diethylenetriamine Pentaacetic Acid," *Science*, 209, 295 (1980). One such method utilizes the formation of a formate ester of the chelating moiety in accordance with the chemical equation:

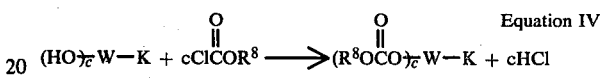

Equation IV wherein R$^8$ is a lower alkyl group having 1 to 4 carbon atoms, such as isobutyl. The reaction is carried out using approximately equimolar quantities of chelating moiety and the formate ester in an anhydrous polar aprotic solvent such as acetonitrile in the presence of a base, preferably an organic tertiary amine. The carbonate ester obtained, after removal of by-product tertiary amine hydrochloride, is then caused to react by addition to an aqueous solution of heparin amine while maintaining the reaction mixture at 0° to 25° C. and a pH of 9 to 9.5 by the addition of an aqueous base such as sodium bicarbonate. Generally, from about 0.5 to 5.0 parts, preferably 0.8 to 1.2 parts by weight of the carbonate ester per part by weight of heparin amine is used. The reaction occurs in accordance with the chemical equation:

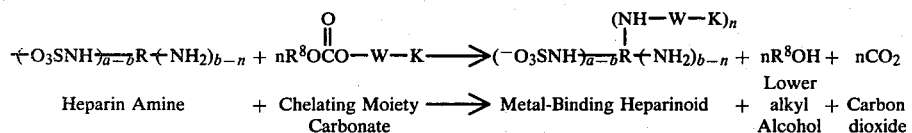

Equation V

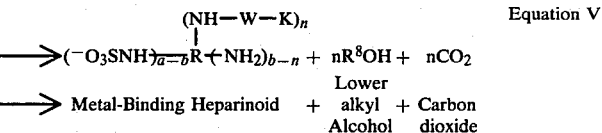

The metal-binding heparinoid compound can then be isolated by dialysis to remove low molecular weight materials, and water is then removed by vacuum distillation, or preferably water is removed by freeze drying.

A second suitable method for preparing the metal-binding heparinoid compound utilizing chelating moieties, (HO$\rightarrow$)$_c$W-K, in which c is one, involves a dehydration reaction in which hydroxyl from the acid group of the chelating moiety and hydrogen from an amino group of heparin amine are eliminated by use of dehydrating agents such as the carbodiimides, e.g., 1-(3-dimethylaminopropyl)-3-ethylcarbodiimide, dicyclohexylcarbodiimide, and 1-cyclohexyl-3-(2-morpholinoethyl)carbodiimide; pyrophosphates, e.g., tetraethyl pyrophosphate; diethyl cyanophosphonate, e.g., (C$_2$H$_5$O)$_2$P(O)CN; and diphenyl phosphorazidate, e.g., (C$_6$H$_5$O)$_2$P(O)N$_3$. The reaction is generally carried out in an aqueous medium utilizing about one to four parts by weight of the dehydrating agent per part of each heparin amine and acid group-containing multidentate compound. The reactants are maintained at 0° to 30° C. for 2 to 24 hours or longer. The metal-binding heparinoid compound can then be isolated as described above using dialysis followed by evaporation of water.

Suitable chelating moieties, (HO—$_c$W-K, where c is one and the coordinating ligand is (c), for use in the preparation of metal-binding heparinoid compounds in accordance with Equation II, are amino carboxylic acids having a coordinating ligand in a side-chain and having the general formula

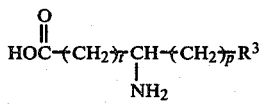

in which t is 0 or 1 and p and $R^3$ are defined above. Exemplary amino acids include serine, cysteine, asparagine, lysine, glutamine, theonine, arginine, histidine, tryptophan, citrulline, hydroxylysine and β-lysine.

The chelating moieties (c) are coupled with heparin amine in accordance with Equation II by first blocking the amino groups of the amino acid (c) moieties in accordance with the methods commonly used in peptide synthesis:

Equation VI

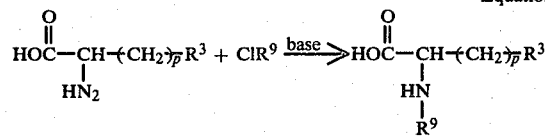

in which p and $R^3$ are defined above, and $R^9$ is a group selected from

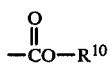

in which $R^{10}$ is selected from benzyl, tert-butyl, or isobutyl and trifluoroacetyl, or triphenylmethyl. The blocked amino acid is then coupled with heparin amine in accordance with methods commonly used in peptide synthesis as has been described above for the coupling of chelating moieties (a) and (b). The blocking group is then readily removed from the coupled reaction product by catalytic hydrogenation or by hydrolysis or saponification.

Suitable chelating moieties, (HO—$_c$W-K, where c is one and the coordinating ligand is (d), for use in the preparation of metal-binding heparinoid compounds in accordance with Equation II include glycolic acid, lactic acid, methoxyacetic acid, 3-ethoxypropionic acid, n-butoxyacetic acid,

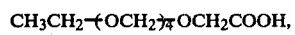

CH$_3$CH$_2$—(OCH$_2$)$_x$OCH$_2$COOH,

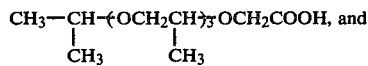

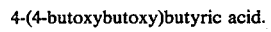

4-(4-butoxybutoxy)butyric acid.

Suitable chelating moieties where c is one and the coordinating ligand is (e) include acetoxyacetoacetic acid, 3-acetoxypropionylpropionic acid, butyryloxyacetoacetic acid, butyrylthioxyacetoacetic acid, and butyramidoacetoacetic acid.

Chelating moieties, (HO—)$_c$W-K, where c is one and the coordinating ligand is (d) or (e), are coupled with heparin amine in accordance with Equation II by methods as described earlier for coupling chelating moieties, (HO—)$_c$W-K where c is one and the cordinating ligand is (a) or (b).

A third method for preparing the metal-binding heparinoid compounds utilizing chelating moieties, (HO—)$_c$W-K, where c is 0, also in accordance with Equation II, employs cyclic anhydrides having a coordinating ligand-containing substituent [these moieties provide the coordinating ligands (e) and (f)]. Examples of such chelating moieties are succinic anhydride, maleic anhydride, 2-acetyloxysuccinic anhydride; 2-acetamidosuccinic anhydride, butyrylamidosuccinic anhydride, 2-acetamidoglutaric anhydride, 2-acetylthiosuccinic anhydride, 2,3-diacetamidosuccinic anhydride, 3-acetamidophthalic anhydride, hemimellitic anhydride, 3-dimethylaminophthalic anhydride, 2,3-pyridindeicarboxylic anhydride, and 3,4-pyridinedicarboxylic anhydride. Generally, the reaction can be carried out by adding to a 2 to 10% aqueous solution of heparin amine from about 0.8 to 1.2 parts of ligand-containing anhydride per part of heparin amine while maintaining the pH at about 9 to 9.5 by the addition of aqueous sodium bicarbonate. Preferably, the ligand-containing anhydride is added as a 5 to 25 percent solution in an aprotic polar solvent such as acetonitrile. Although the reaction is quite rapid, it is generally desirable to maintain reaction conditions at 0° to 30° C. for a period of one to five hours. As for the previously described methods of preparation, the metal-binding heparinoid compound can be isolated by using dialysis to remove low molecular weight materials and freeze drying to remove water.

A fourth method for preparing metal-binding heparinoid compounds by coupling heparin amine to a chelating moiety, (HO—)$_c$W-K, in accordance with Equation II, in which c is 0, W is

and K is -SH, involves maintaining for about 5 to 100 hours or more at 0° to 30° C. under an inert atmosphere, while agitating, a 2 to 10 percent solution of heparin amine in a 0.1 to 0.5 molar basic solution, which preferably is a 0.3 molar solution of a tertiary amine such as trimethylamine, using from about 1 to 10 parts of carbon disulfide per part of heparin amine. The metal-binding heparinoid compound can be isolated after dialysis to remove low molecular weight materials by evaporation of water.

The heparin amine derivative may be coupled with one or two different chelating moieties in preparing the metal-binding intermediate heparinoid compound. By judiciously balancing the ratio and kind of chelating moiety, one may affect the affinity of the radio-labeled heparinoid to the thrombus. Combinations of polyacetic acid amine derivatives with the dithio derivatives appear to be advantageous.

As indicated previously, the metal-binding heparinoid compound may be coupled with one of many radioactive ions, e.g., $^{111}$In, $^{51}$Cr, $^{68}$Ga, and $^{99m}$Tc, by conventional techniques.

The $^{99m}$Tc used in this invention is obtainable from a $^{99}$Mo generator in the conventional manner. Eluting or "milking" the generator with an aqueous medium will provide the 99m-pertechnetate solution in the form of $M^{+x}(^{99m}TcO_4^-)_x$, where $M^{+x}$ is a pharmaceutically acceptable cation such as a proton, an alkali metal ion, an ammonium ion, or the like, and x is a positive integer less than 4. Typically, the aqueous elution medium is a saline solution, which provides sodium 99m-pertechnetate.

The pertechnetate ion can be reduced chemically or electrolytically to a lower oxidation state of technetium, preferably by reaction with an oxidizable low valence metal salt such as a tin (II) salt (e.g. $SnCl_2$ or $NaSn_2F_5$), an iron (II) salt (e.g. a ferrous salt/ascorbic acid medium), a Cu(I)/Cu(II) couple, a combination thereof, or other chemical reducing agents such as mercaptans, metal hydrides, thiosulfates or hypophosphites. A particularly suitable means for providing the reducing agent and the heparinoid compound is to preformulate a radiopharmaceutical kit for use with the $^{99}Mo$ generator. For example, 0.1 (preferably at least 0.5) to 10 ml. of a solution containing about 0.5 to about 1000 micromole/ml of heparinoid compound and a suitable amount, e.g. 0.01–100 micromoles/ml of reducing agent can be hermetically and aseptically sealed in separate vials or the same vial. A preservative such as benzyl alcohol is optionally included in the contents of the vial. The solution in the vial is preferably substantially isotonic with mammalian body fluids, e.g., human blood. The contents of the vial can be combined with the pertechnetate-containing, substantially isotonic eluate, mild heat can be applied if necessary to the combined solutions to achieve the reduction and Tc-complex formation, and the resulting radio-pharmaceutical can then be injected into the blood stream of the patient or test animal. Radioactivity measurements are made in a conventional manner for a period from the time of injection until about 5 to 10 hours afterwards, depending on the nature of the study or diagnosis. Most studies call for at least one half hour of post injection radioactive measurements. These measurements can be corrected for decay in the usual manner and studied with a view toward obtaining a picture of a formed or forming blood clot.

The amount of $^{99m}Tc$ needed to produce an amount of radiopharmaceutical suitable for most diagnostic or research uses is extremely small and is generally in the range of about 0.01 millicuries per milliliter (mC/ml) of 99m-pertechnetate solution up to about 500 mC per ml of such solution. Only about $0.03 \times 10^{-10}$ gram of 99m-pertechnetate dissolved in a milliliter of aqueous medium (e.g. isotonic saline) is needed to provide 0.01 mC/ml, and less than $100 \times 10^{-10}$ gram of 99m-pertechnetate per milliliter of solution provides enough radioactivity for most uses. Due to the short half-life of the $^{99m}Tc$ it is preferred to prepare small batches of 99m-pertechnetate solution for immediate use. Batches as small as 0.1 ml can be adequate for animal studies (e.g. for injection in mice) and batches as large as 50 ml are convenient for one or more injections in one or a group of human patients.

The $^{111}In$ derivative of the metal-binding heparinoid intermediate product is formed by the direct reaction of carrier-free 111-indium chloride with the metal-binding heparinoid, as described above. The reaction is very effective in that better than 90% of the applied indium is bound in this simple manner (see EXAMPLE 14).

The diagnosis of suspected deep vessel thrombosis is easily and simply accomplished according to the present invention. A patient is intravenously injected with less than 1.0 mg/kg of body weight in a physiologically acceptable medium, such as saline solution, of the radiolabeled heparinoid compound prepared as in EXAMPLE 14 or 18 and scanned within a few minutes up to about 10 hours using-imaging equipment. A positive radiographic image resulting from an accumulation of radio-labeled material indicates the size and location of a forming or formed blood clot and provides valuable information for the attending physician.

To determine the effectiveness of the radio-labeled heparinoid compound in adsorbing on a thrombus, partially occlusive arterial and venous thrombi were induced in rats and rabbits (see EXAMPLES 19 and 20). Shortly after formation of the thrombus, the diagnostic agent was administered through the jugular vein. Later, the thrombus and the thrombosed vessel were removed and a count of radioactivity was made. In this manner it was determined that the radio-labeled heparinoid compounds of this invention were preferentially adsorbed on a formed thrombus as opposed to undamaged vessel walls. EXAMPLE 21 illustrates the facility with which images of thrombi can be obtained.

Objects and advantages of this invention are further illustrated by the following examples, but the particular materials and amounts thereof recited in these examples, as well as other conditions and details, should not be construed to unduly limit this invention.

EXAMPLE 1

Preparation of sodium heparin amine

Sodium heparin was converted to the pyridinium salt by passing 270 ml of 7.5% (W/V) solution through 200 ml of Amberlite IR-120 ® cation exchange resin ($H^+$ form) in a $2.5 \times 75$ cm column and washing with distilled water until the effluent was neutral. An excess of pyridine (25 ml) was added to the heparinic acid collected, and the solution was then lyophilized. The yield was 22.1 grams. The pyridinium heparin was then dissolved in 330 ml of dimethyl sulfoxide (DMSO) containing 5 volume percent water. The solution was stirred and heated to 50° C. After two hours the solution was cooled to room temperature and 50 ml of 10% (W/V) NaCl solution was added. The mixture was added dropwise to 4.0 liters of acetone and stirred for 15 minutes. The precipitate was collected by filtration, dissolved in 150ml of 10% W/V NaCl solution and reprecipitated in 3.0 liters of acetone. This precipitation process was repeated and the solid produced was filtered and dried under vacuum. The mixture of NaCl and heparamine (N-desulfated heparin) was dissolved in 200 ml of water and diafiltered against water using an ultrafiltration cell fitted with a 1000 MW cutoff membrane until the filtrate did not cause silver ion to precipitate from 0.1 M $AgNO_3$ solution. The solution was then lyophilized producing 11.3 g of sodium heparamine.

Variation of reaction time and temperature (not to exceed 50° C.) of the pyridinium salt of heparin in DMSO-water solution produced varying degrees of N-desulfation reaction. See TABLE I, below. The extent of reaction was determined by comparison of the intensities of the G-1, G-2 and G-6 peaks present in the $^{13}C$ nmr spectrum of the product. These peaks were significantly shifted upon reaction while other features of the spectrum of heparamine were increased in complexity and have not been assigned.

TABLE I

| Time | Temperature | Percent N-desulfation |
|---|---|---|
| 20 min. | 25° C. | 20 |
| 2 hrs. | 25° C. | 50 |
| 2 hrs. | 50° C. | 100 |

EXAMPLE 2

Coupling the chelating moiety to the heparin amine compound using method 1

A slight excess of triethylamine, 1.35 g, was used to neutralize 1.0 g of diethylenetriaminepentaacetic acid (DTPA) in 10 ml of water with stirring and warming. The solution was lyophilized and dissolved in 10.0 ml of dry acetonitrile. The solution was then cooled in an ice bath and 0.35 g of isobutyl chloroformate in 3.0 ml of dry acetonitrile was added dropwise. After stirring the mixture for 30 minutes, the precipitate was collected by filtration and the filtrate was added dropwise to a solution of 1.0 g of sodium heparamine from EXAMPLE 1, in 25 ml of 5% (W/V) NaCl solution at 0° C. The pH of the heparamine solution was maintained in the range of 9.0–9.5 during a 15 minute addition and for an additional 4 hours with 0.2 M $NaHCO_3$ solution. The reaction mixture was lyophilized, redissolved in 10% (W/V) salt solution, and diafiltered against water until the filtrate was salt-free as described in EXAMPLE 1. The retentate was then lyophilized to yield 0.96 g of heparin-DTPA. The $^{13}C$ nmr spectrum of the product contained peaks unambiguously assigned to DTPA which were broadened and slightly shifted in accordance with being bound to a polymer. The unassigned heparamine multiplet also showed changes upon reaction, but was not interpreted.

EXAMPLE 3

Using the method of EXAMPLE 2, ethylenediaminetetraacetic acid (EDTA) was coupled to heparin.

EXAMPLE 4

Using the method of EXAMPLE 2, cyclohexyldiaminetetraacetic acid (CyDTA) was coupled to heparin.

EXAMPLE 5

Using the method of EXAMPLE 2, diethylenetriaminepentamethylenephosphonic acid (DTPMP) was coupled to heparin.

EXAMPLE 6

Coupling the chelating moiety to the heparin amine compound using method 3

A solution of 1.0 g of succinic anhydride in 10 ml of dry acetonitrile was added dropwise over 15 to 30 minutes to 1.0 g of sodium heparamine from EXAMPLE 1 in 25 ml of 5% NaCl solution at room temperature. The pH of the reaction mixture was maintained at 9.0–9.5 by addition of 0.2 M $NaHCO_3$ as needed over a two hour period. The resulting solution was lyophilized and diafiltered against water as in EXAMPLE 1 until the filtrate was salt-free. The product, heparin-succinamide, was isolated by lyophilization of the retentate, 0.85 g. The reaction was also carried out by adding succinic anhydride as the solid, in four 0.25 g portions. The $^{13}C$ nmr spectrum of the product showed peaks assigned to a succinamide moiety in addition to those of heparamine. The multiplet peaks were also changed in shift and intensity in the reaction product, but were not assigned.

EXAMPLE 7

Using the method of EXAMPLE 6, pyridine-2,3-dicarboxylic anhydride produced heparin pyridine-2,3-carboxamide carboxylic acid (heparin-PCC).

EXAMPLE 8

Using the method of EXAMPLE 6, 2-acetylthiosuccinic anhydride produced heparin 2-acetylthiosuccinamide.

EXAMPLE 9

Using the method of EXAMPLE 6, 2-acetylamidosuccinic anhydride produced heparin N-acetylaspartamide.

EXAMPLE 10

Coupling the chelating moiety to the heparin amine compound using method 4

Sodium heparamine from EXAMPLE 1, 1.0 g, was dissolved in 30 ml of 0.3 M trimethylamine solution. Carbon disulfide ($CS_2$), 1.0 ml, and 1.5 g of NaCl were added and the mixture was stirred under a nitrogen atmosphere at room temperature. After 24 hours another 1.0 ml of $CS_2$ was added and stirring was continued for another 96 hours. A stream of nitrogen gas was bubbled through the reaction mixture for 15 minutes to remove excess $CS_2$. The product was isolated by diafiltration against 1500 ml of 10% salt solution followed by water in an ultrafiltration cell fitted with a 1000 MW cutoff membrane until the filtrate produced no AgCl precipitate when added to 0.1 M $AgNO_3$. The retentate was lyophilized to yield 1.04 g. The $^{13}C$ nmr of the reaction product contained a new peak compatible with a dithiocarbamate product. The multiplet peaks of heparamine were also significantly changed, but have not been assigned.

EXAMPLE 11

Coupling the chelating moiety to the heparin amine compound using method 2

Sodium heparamine was coupled to Nα-carboxybenzyl-L-arginine (N-CBZ-arginine) by adding two 0.5 g portions of 1-(3-dimethylaminopropyl)-3-ethylcarbodiimide hydrochloride (EDC) to a solution of 1.0 g of sodium heparamine and 1.0 g of N-CBZ-arginine in 25 ml of 5% (W/V) salt solution at pH 7.0–7.5 over a one hour period. The pH of the reaction mixture was maintained by additions 0.1 M HCl as needed for a total of 16 hours. The product of the reaction was isolated by diafiltration against water as in EXAMPLE 1. Lyophilization of the retentate produced 1.02 grams. The $^{13}C$ nmr of the isolated product contained peaks assigned to N-CBZ-arginine which were broadened in agreement with being coupled to the heparamine polymer. Heparamine peaks also showed changes, but have not been assigned.

EXAMPLE 12

Preparation of a mixed-ligand heparinoid compound

Using the method of EXAMPLE 2 combined with the method of EXAMPLE 6, a mixed heparin derivative was prepared. A solution of succinic anhydride as in EXAMPLE 6 was added to a heparamine solution one hour after the carboxylic-carbonic anhydride reagent of EXAMPLE 2. After four hours the product of these reactions was isolated by successive diafiltration against 800 ml of 10% (W/V) NaCl and water until the filtrate was free of salt as in EXAMPLE 1. Lyophilization of the retentate produced 0.90 grams. The $^{13}C$ nmr spectrum of this product indicated that both DTPA and succinamide moieties were present. Peaks assignable to these groups as in EXAMPLES 2 and 6 plus a complex herparamine multiplet were present.

EXAMPLE 13

Preparation of a mixed-ligand metal-binding heparinoid compound

Using the method of EXAMPLE 2 with the exception of a shorter reaction time of one hour and the method of EXAMPLE 11 with the exception that the isolated product of the reaction was used in place of sodium heparamine, a heparin-DTPA-CS$_2$ derivative was isolated, 0.54 grams. Resonances previously seen for the separate moieties, dithiocarbamate and DTPA, were evident in the $^{13}C$ nmr spectrum of this product. Also, a very complex heparamine multiplet was present which was reasonable for this mixed derivative.

EXAMPLE 14

Chelation of the intermediate metal-binding heparinoid compound with a radioactive metal ion Heparin-DTPA was dissolved in 0.9% W/V saline solution at a concentration of 10.0 mg/ml, pH 4.0–5.0. Carrier-free 111-indium chloride, 2 mC/ml activity, was added slowly to the heparamine solution to a final activity of 0.2 mC/ml. This solution was stirred at room temperature for one hour before the pH of the mixture was adjusted to 7.2–7.4 with 0.2 M NaHCO$_3$. The extent of In$^{+3}$ bound to the heparin-DTPA derivative was determined by electrophoresis in agarose, pH 3.0. Heparin-DTPA was located by staining the electrophoresis plate with 0.1% (W/V) toluidine blue. The labeling efficiency was determined by the ratio of the amount of radioactivity associated with the heparin-DTPA stain relative to the total amount on the plate, and was found to be 97.0%. The stability of the heparin-DTPA·$^{111}$In material was determined by adding 50 microliters of labeled solution to 0.50 ml of normal human plasma and incubating it for one hour at 40° C. The amount of radioactive tracer which remained bound to heparin-DTPA was determined as above by electrophoresis, and was found to be 92.3%. This data indicated that the heparin DTPA derivative bound 111-indium efficiently and the complex was stable in contact with plasma proteins.

EXAMPLE 15

Using the method of EXAMPLE 14, heparin-CS$_2$ labeled with $^{111}$InCl$_3$.

EXAMPLE 16

Using the method of EXAMPLE 14, heparin-arginine was labeled with $^{111}$InCl$_3$.

EXAMPLE 17

Using the method of EXAMPLE 14, heparin-PCC was labeled with $^{111}$InCl$_3$.

EXAMPLE 18

Heparin-CS$_2$ was dissolved in 0.9% W/V saline solution at a concentration of 5.0 mg/ml, pH 2.5, and 0.5 milliliters of sodiumpentafluorodistannate(II) solution, 0.7 microgram/ml, was added. 99m-Technetium, in the pertechnetate form (TcO4-), was then added to a total activity of 0.5 mC and the mixture stirred under nitrogen for 15 minutes. The pH of the solution was then adjusted to 7.2–7.4 with 0.2 M NaHCO$_3$. The extent to which 99m-technetium was bound to heparin-CS$_2$ and the stability of that binding, determined by the methods of EXAMPLE 14, were 94.0 and 82.6% respectively. This indicates that heparin-CS$_2$ does bind 99m-technetium and that this compound is stable in contact with plasma proteins.

EXAMPLE 19

Partially-occlusive arterial thrombosis data

Rats, anesthetized with sodium pentobarbital, had their neck region opened to expose both carotid arteries and one jugular vein. A PE-50 polyethylene catheter, tipped with a 23 gauge needle, was inserted into the jugular vein and secured to the surrounding tissue. A partially-occlusive thrombus was created in one of the arteries by the passage of one milliamp of electrical current for 30 seconds across the artery using stainless steel electrodes.

One-half hour following the start of electrical stimulation, the $^{111}$In-heparinoid compound prepared as in EXAMPLE 14, at a dose of 5 mg/kg of body weight, was administered to the animals through the jugular vein catheter in volumes of less than one milliliter. One hour after complex administration, the experiment was terminated by the removal of both carotid arteries. Both vessel segments were blotted gently to remove excess blood and then analyzed for residual γ-radiation. The differences between the two arteries, the thrombosed and non-thrombosed, was determined by using the paired t-test statistics. The data obtained for a variety of $^{111}$In-heparinoid compounds is shown in TABLE II.

TABLE II

| $^{111}$In-Heparinoid Complex | Thrombosed Artery* | Non-Thrombosed Artery* |
|---|---|---|
| heparin-DTPA-$^{111}$In | 1,748 | 832.8 |
| heparin-CS$_2$—$^{111}$In | 2,948.4 | 988.5 |
| heparin-arginine-$^{111}$In | 1,950.0 | 921.2 |
| heparin-PCC$^{(a)}$-$^{111}$In | 256.0 | 107.2 |

*Mean cpm
$^{(a)}$heparin pyridine-2,3-carboxamide carboxylic acid

This data demonstrates that there is a significant (p=B <0.01 accumulation of the $^{111}$In-heparin compounds in the thrombosed artery, when compared to the non-thrombosed artery, and shows that these radiolabeled heparinoid compounds are useful in detecting arterial thrombi.

EXAMPLE 20

Partially-occulsive venous thrombosis data

Four rabbits, anesthetized with sodium pentobarbital, had their neck region opened to expose both jugular veins and one carotid artery. Both veins were isolated from the surrounding tissue and from their feeder veins for a length of approximately four centimeters. A stenosis was created in the vein in which the thrombus was to be formed downstream from the thrombus site while a PE-50 polyethylene catheter, tipped with a 23 gauge needle, was placed into the other jugular vein and secured to the surrounding tissue. One-half hour after the completion of the surgery, a thrombus was created by the injection of 2.0 NIH units of thrombin into the temporarily occluded vein segment. Both the occlusion and the injection needle remained in place for one minute.

One-half hour following the thrombus formation, the heparin-DTPA.$^{111}$In compound was administered, 5 mg/kg dose, through the jugular vein catheter. The experiment was terminated one hour later by tying off and opening both veins, removal of the thrombus and collecting a one-half milliliter blood sample from the exposed carotid artery. Both vein segments, the thrombus and the blood sample were assayed for their residual $\gamma$-radiation level after they were weighed. The data was normalized to counts/min/mg tissue, and all tissues were compared to the blood sample. The differences between the blood and the other tissues were determined by using the Dunnett's t-test. The data is shown in TABLE III.

TABLE III

| Tissue | $\overline{CPM}$/Mg Tissue | Statistics |
|---|---|---|
| Thrombus | 223.0 | p = 0.01 |
| Blood | 89.2 | |
| Thrombosed vein | 139.4 | N. Sig. |
| Non-thrombosed vein | 123.9 | N. Sig. |

$\overline{CPM}$ — Mean counts/min.
N. Sig. — No significant difference

The data demonstrates that the heparin-DTPA.$^{111}$In compound did significantly bind to the preformed venous thrombus but not to the vessel walls. It also demonstrated that the heparin-DTPA.$^{111}$In complex was useful in detecting venous thrombi.

EXAMPLE 21

Venous Thrombosis imaging data

A 20 kilogram dog was anesthetized with pentabarbitol and placed on a respirator. The jugular vein was exposed and a catheter was inserted. Under fluoroscopy the catheter was placed in the femoral vein of one leg. The tip of the guide wire was then exposed for a length of approximately two inches and connected to an electrical stimulator. An electrical current of 600–800 milliamperes at 5–6 volts was used to damage the vessel wall and initiate thrombus formation. The catheter was removed after an hour of stimulation and the thrombus allowed to stabilize for four hours. At that time heparin-DTPA.$^{111}$In compound prepared as in EXAMPLE 15 was injected through a catheter placed in the saphenous vein of the opposite leg at a dose of 0.25 mg/kg. The thrombosed leg was then placed in the field of the gamma camera and images were recorded over the period of an hour. The images showed a target-to-non-target ratio of 15. This is sufficient to easily identify the location and size of the formed thrombus.

Various modifications and alterations of this invention will become apparent to those skilled in the art without departing from the scope and spirit of this invention, and it should be understood that this invention is not to be unduly limited to the illustrative embodiments set forth herein.

We claim:

1. A metal-binding intermediate compound for preparing a radiopharmaceutical for diagnosing blood clots comprising:

(a) a water-soluble polysaccharide moiety having an average of at least 0.25 anionic groups per monosaccharide unit, and (b) at least one chelating group derived from the group consisting of amino acids, substituted cyclic acid anhydrides, and carbon disulfide.

2. The metal-binding intermediate compound according to claim 1 wherein said polysaccharide moiety is derived from the group consisting of homopolysaccharides and heteropolysaccharides.

3. The metal-binding intermediate compound according to claim 2 wherein said heteropolysaccharides are selected from the group consisting of chondroitin sulfates A and C, dermatan sulfate, keratan sulfates I and II, heparan sulfate, and heparin.

4. The metal-binding intermediate compound according to claim 2 wherein said homopolysaccharide is selected from the group consisting of dextran sulfates.

5. The metal-binding intermediate compound according to claim 1 wherein the water-soluble polysaccharide moiety is derived from heparin by desulfation.

6. The metal-binding intermediate compound according to claim 1 wherein the chelating group is derived from the group consisting of diethylenetriaminepentaacetic acid, ethylenediaminetetraacetic acid, cyclohexyldiamine tetraacetic acid, diethylenetriaminepentamethylene phosphonic acid, carbon disulfide, and substituted succinic anhydrides.

7. A radiopharmaceutical compound for diagnosing blood clots formed by the a reaction of:

(a) a metal-binding intermediate compound comprising: (1) a water-soluble polysaccharide moiety having an average of at least 0.25 anionic groups per monosaccharide unit, and (2) at least one chelating group, and (b) a radioactive tracer metal compound.

8. The radiopharmaceutical compound according to claim 7 wherein the radioactive tracer metal compound is a $^{111}$In, $^{99m}$Tc, $^{51}$Cr or $^{68}$Ga compound.

9. The radiopharmaceutical compound according to claim 7 wherein the radioactive tracer metal compound is a $^{111}$In compound.

10. The radiopharmaceutical compound according to claim 7 wherein the radioactive tracer metal compound is a $^{99m}$Tc compound.

11. A method for diagnosing and locating a formed or forming blood clot in a mammal comprising the steps:

(a) injecting intravenously said mammal with less than about 1.0 mg/kg of the radiopharmaceutical compound, according to claim 8, in a physiologically acceptable medium, and (b) examining said mammal with $\gamma$-imaging or scintillographic equipment.

12. A metal-binding heparinoid intermediate compound for diagnosing blood clots comprising a reaction product of:

(a) a heparin amine moiety, formed by the removal of 10 to 100% of the N-sulfate groups of heparin salt, and (b) at least one chelating group derived from the group consisting of amino acids, substituted cyclic acid anhydrides, and carbon disulfide.

13. The metal-binding heparinoid intermediate compound according to claim 12 wherein the heparin amine moiety is formed by the removal of 30 to 70% of the N-sulfate groups on the heparin salt.

14. The metal-binding heparinoid intermediate compound according to claim 12 wherein the heparin amine moiety is formed by the removal of 40 to 60% of the N-sulfate groups on the heparin salt.

15. The metal-binding heparinoid intermediate compound according to claim 12 wherein the chelating group is derived from the group consisting of diethylenetriaminepentaacetic acid, ethylenediaminetetraacetic acid, cyclohexyldiamine tetraacetic acid, diethylenetriaminepentamethylenephosphonic acid, carbon disulfide, and substituted succinic anhydrides.

16. The metal-binding heparinoid intermediate compound according to claim 12 wherein up to 100% of the N-sulfate groups on the heparin salt have been removed and wherein the chelating group is derived from DTPA.

17. The metal-binding heparinoid intermediate compound according to claim 12 wherein up to 100% of the N-sulfate groups on the heparin salt have been removed and wherein the chelating group is derived from $CS_2$.

18. A radio-labeled heparinoid compound for diagnosing blood clots formed by the reaction of
   (a) a metal binding heparinoid intermediate compound comprising:
      (1) a heparin amine moiety, formed by the removal of 10 to 100% of the N-sulfate groups of heparin salt, and
      (2) at least one chelating group, and
   (b) a radioactive tracer metal compound.

19. The radio-labeled heparinoid compound according to claim 18 wherein the radioactive tracer metal compound is a $^{111}$In, $^{99m}$Tc, $^{51}$Cr or $^{68}$Ga compound.

20. The radio-labeled heparinoid compound according to claim 18 wherein the radioactive tracer metal compound is a reduced pertechnetate compound.

21. A metal-binding heparinoid compound having the formula:

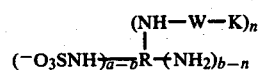

wherein:
   a and b are numbers having a value from about 5 to 50 and b is less than or equal to a;
   R is the residue of heparin salt devoid its $NHSO_3^-$ groups;
   n is a number having a value of 1 to 50;

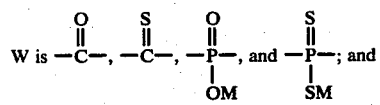

K is a coordinating ligand selected from the groups consisting of:
   (a) $(CH_2)_pN{-(R^1)}_2$
in which:
   each $R^1$ is independently selected from the group consisting of
      (1) hydrogen,
      (2) $-(CH_2)_pY$, in which Y is

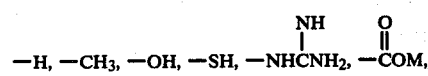

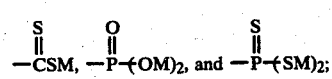

(3) $-(CH_2)_pN{-(R^1)}_2$, and
   p is an integer of 1 to 3, and
   M is hydrogen, an alkali metal ion, ammonium ion or a lower alkyl group having 1 to 4 carbon atoms,
with the proviso that K contains no more than 4 nitrogen atoms and no nitrogen atom in K has more than one $-(CH_2)_pY$ groups in which Y is $-H$ or $-CH_3$;

(b)

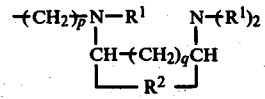

in which:
   p and $R^1$ are as defined in (a), q is 0 or 1 to 3, and
   $R^2$ is a divalent group having 2 to 6 carbon atoms, of which one carbon atoms can be replaced by $-O-$, $-S-$, or $-NH-$, which atoms are necessary in order to form a ring with $-CH{-(CH_2)_q}CH-$, the ring having 5 to 8 nuclear atoms that can be saturated or unsaturated and optionally substituted by $-(CH_2)_qY$ groups in which Y is as defined in (a) and q is 0 or 1 to 4;

(c)

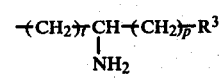

in which: t is an integer of 0 or 1,
   p is an integer of 1 to 3,
   $R^3$ is a group selected from $-OH$, $-SH$,

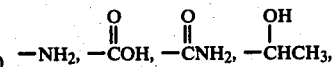

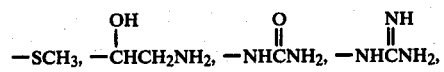

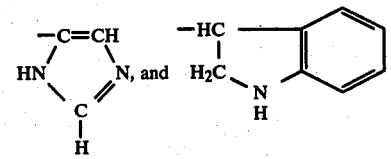

(d) $-{[(CH_2)_rO]}_sR^4$
in which:
   r and s are independently integers of 1 to 4, and
   $R^4$ is hydrogen or lower alkyl of 1 to 4 carbon atoms;

(e)

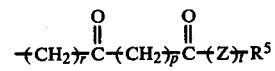

in which:
   r, p, and t are integers of 1 to 4, 1 to 3, and 0 or 1 respectively, Z is $-O-$, $-S-$, or $-NH-$, and
   $R^5$ is a lower alkyl group having 1 to 4 carbon atoms;

(f)

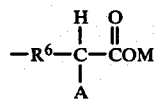

in which:

R[6] is alkylene or alkenylene having 1 to 4 carbon atoms,

M is as defined in (a), and

A is

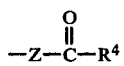

in which R[4] and Z are as defined in (d) and (e) respectively; and (g)

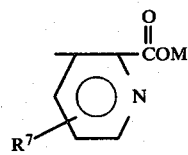

in which: R[7] is $-(CH_2)_q-Y$ in which q is 0 or 1 to 4 and Y and M are as defined in (a).

22. A radio-labeled heparinoid compound comprising a reaction product of the metal-binding heparinoid compound according to claim 21 and a radioactive metal compound.

23. A method for diagnosing and locating a formed or forming blood clot in the vascular system of a mammal comprising the steps:
   (a) injecting intravenously said mammal with less than about 1.0 mg/kg of the radio-labeled heparinoid compound, according to claim 22, in a physiologically acceptable medium, and
   (b) examining said mammal with γ-imaging or scintillographic equipment.

24. A compound comprising:
   (a) a water-soluble polysaccharide moiety having an average of at least 0.25 anionic group per monosaccharide unit, and
   (b) at least one chelating group derived from the group consisting of amino acids, substituted cyclic acid anhydrides, and carbon disulfide.

25. A compound comprising the reaction product of:
   (a) a compound comprising: (1) a water-soluble polysaccharide moiety having an average of at least 0.25 anionic group per monosaccharide unit, and (2) at least one chelating group, and
   (b) a radioactive tracer metal compound.

* * * * *